(12) United States Patent
Cipriani et al.

(10) Patent No.: US 9,731,289 B2
(45) Date of Patent: Aug. 15, 2017

(54) AUTOMATION OF INCUBATION, PROCESSING, HARVESTING AND ANALYSIS OF SAMPLES IN A MULTI-CELL PLATE WITH THIN FILM SAMPLE SUPPORT

(71) Applicant: EUROPEAN MOLECULAR BIOLOGY LABORATORY, Heidelberg (DE)

(72) Inventors: Florent Cipriani, Claix (FR); Jose Antonio Marquez, La Riviere (FR)

(73) Assignee: EUROPEAN MOLECULAR BIOLOGY LABORATORY, Heidelberg (DE)

( * ) Notice: Subject to any disclaimer, the term of this patent is extended or adjusted under 35 U.S.C. 154(b) by 32 days.

(21) Appl. No.: 14/653,727

(22) PCT Filed: Dec. 18, 2013

(86) PCT No.: PCT/EP2013/077171
§ 371 (c)(1),
(2) Date: Jun. 18, 2015

(87) PCT Pub. No.: WO2014/096055
PCT Pub. Date: Jun. 26, 2014

(65) Prior Publication Data
US 2015/0321190 A1    Nov. 12, 2015

Related U.S. Application Data

(60) Provisional application No. 61/738,506, filed on Dec. 18, 2012.

(51) Int. Cl.
*B01L 3/06*    (2006.01)
*B01L 3/00*    (2006.01)
(Continued)

(52) U.S. Cl.
CPC ............... *B01L 3/06* (2013.01); *B01L 3/5085* (2013.01); *B01L 3/50853* (2013.01);
(Continued)

(58) Field of Classification Search
CPC ........... B01L 2200/025; B01L 2200/10; B01L 2300/044; B01L 2300/0893;
(Continued)

(56) References Cited

U.S. PATENT DOCUMENTS 6,913,732 B2 *  7/2005  Sha ........................ B01L 3/5025
                                             117/206
7,807,108 B2 * 10/2010  Fasulka ................. B01L 3/5025
                                             422/400

(Continued)

FOREIGN PATENT DOCUMENTS

JP    2005-77308 A       3/2005
WO    WO 03/087326 A2   10/2003

OTHER PUBLICATIONS

Cipriani et al., "CrystalDirect: a new method for automated crystal harvesting based on laser-induced photoablation of thin films", Biological Crystallography, Acta Cryst. (2012), D68, pp. 1393-1399.

(Continued)

*Primary Examiner* — Maureen Wallenhorst
(74) *Attorney, Agent, or Firm* — Birch, Stewart, Kolasch & Birch, LLP (57) ABSTRACT

The present invention relates to the automation of incubation, processing, harvesting and analysis of samples in a multi-cell plate. In particular, a multi-cell plate including a body with a plurality of cells is presented. Furthermore, an automated crystal harvesting and processing system with a cutting unit, a fluid unit and a removing device is presented. The multi-cell plate further includes a sealing film for (Continued)

sealing the cells on a first side of the body and a sample film for sealing the cells on a second side of the body. The sample film is adapted for accommodating a biological material for crystallization. Furthermore, the sample film is of a thickness and composition that makes it compatible with x-rays and also with laser ablation. The design of the multi-cell plate and the automated crystal harvesting and processing system allows for several steps of incubation, processing, harvesting and analysis of the samples to be automated.

15 Claims, 6 Drawing Sheets (51) Int. Cl.
    G01N 1/04       (2006.01)
    G01N 35/10      (2006.01)
    G01N 35/00      (2006.01)
    G01N 35/02      (2006.01)
    C12M 1/32       (2006.01)
    C12M 1/34       (2006.01)
    C12M 1/36       (2006.01)
    G01N 35/04      (2006.01)

(52) U.S. Cl.
    CPC ............ *C12M 23/12* (2013.01); *C12M 41/36* (2013.01); *C12M 41/48* (2013.01); *G01N 1/04* (2013.01); *G01N 35/0099* (2013.01); *G01N 35/028* (2013.01); *G01N 35/10* (2013.01); *G01N 35/1079* (2013.01); *B01L 2200/025* (2013.01); *B01L 2200/10* (2013.01); *B01L 2300/044* (2013.01); *B01L 2300/0893* (2013.01); *B01L 2300/12* (2013.01); *B01L 2300/16* (2013.01); *G01N 2001/045* (2013.01); *G01N 2035/0403* (2013.01)

(58) Field of Classification Search
    CPC .... B01L 2300/12; B01L 2300/16; B01L 3/06; B01L 3/5085; B01L 3/50853; C12M 23/12; C12M 41/36; C12M 41/48; G01N 1/04; G01N 2001/045; G01N 2035/0403; G01N 35/0099; G01N 35/028; G01N 35/10; G01N 35/1079
    USPC ........... 436/4, 43, 63, 86, 94, 164, 165, 174; 422/63, 67, 68.1, 82.05, 509, 512, 547, 422/552, 559; 435/288.4, 288.7
    See application file for complete search history.

(56) References Cited

U.S. PATENT DOCUMENTS

| 2004/0096368 | A1  | 5/2004 | Davis et al. |
| 2004/0141895 | A1* | 7/2004 | Sha .......................... C30B 7/00 422/245.1 |
| 2005/0056205 | A1  | 3/2005 | Goodwin, Jr. |
| 2006/0045421 | A1* | 3/2006 | Baets ................... G02B 6/4201 385/33 |
| 2008/0234140 | A1  | 9/2008 | Kuoni |
| 2012/0021523 | A1* | 1/2012 | Fowler ............. G01N 23/20025 436/4 |

OTHER PUBLICATIONS

Viola et al., "First experiences with semi-autonomous robotic harvesting of protein crystals", J Struct Funct Genomics (2011) 12, pp. 77-82.

Viola et al., "Operator-assisted harvesting of protein crystals using a universal micromanipulation robot", Journal of Applied Crystallography, (2007), 40, pp. 539-545.

* cited by examiner

AUTOMATION OF INCUBATION, PROCESSING, HARVESTING AND ANALYSIS OF SAMPLES IN A MULTI-CELL PLATE WITH THIN FILM SAMPLE SUPPORT

CROSS REFERENCE TO RELATED APPLICATIONS

This application is the National Phase of PCT/EP2013/077171 filed on Dec. 18, 2013, which claims priority under 35 U.S.C. 119(e) to U.S. Provisional Application No. 61/738,506 filed on Dec. 18, 2012, all of which are hereby expressly incorporated by reference into the present application.

FIELD OF THE INVENTION

The present invention relates to a multi-cell plate for automated incubation, processing, harvesting and analysis of samples of biological material. Furthermore, the present invention relates to an automated system for incubation, processing, harvesting and analysis of samples of biological material. Moreover, the present invention relates to a method of operating the automated system.

BACKGROUND OF THE INVENTION

Macromolecular crystallography may be used both in academia and industry for structural analysis of biological molecules and to help in the development of therapeutic and other bioactive molecules. For this purpose samples are mixed with solutions containing components that are likely to induce crystal formation in multi-cell plates. Crystals need to be exposed to powerful x-ray beams to extract structural information.

Multi-cell plates used for macromolecular crystallography, e.g. for protein crystallisation, comprise a plurality of cells. Different samples with biological material may be incubated in different crystallization solutions into the different cells or chambers of the multi-cell plate. Crystals may take from hours to several weeks to appear, during which time multi-cell plates are stored at constant temperature and inspected regularly under a microscope with visible or UV light.

Crystals may be exposed to x-rays directly in multi-cell plates. However this produces a high level of background due to interference produced by the material of the multi-cell plate, decreasing the quality of the data. More often crystals are extracted out of the multi-well plate with a specific tool (a cryo-loop) working under a microscope. This eliminates the interference from the multi-cell plate material and reduces the amount of crystallization solution around the crystal that may also interfere with the measurement. X-ray experiments are often performed at cryogenic temperature (100 Kelvin for example). Crystals are often also stored and transported at this temperature. Thus, it may often be necessary to provide the crystals with cryo protection for further storage, transport or for analysis, e.g. by x-ray diffraction. For this purpose each sample has to be removed from the plate and incubated with a solution containing a cryo protectant agent.

Furthermore, for some applications it may be necessary to deliver to the crystals additional components such as ligands. Also in this case samples, e.g. crystals, are extracted from the solution in which they grow and transferred to solutions containing those chemical agents. This process is also denoted as soaking (ligand soaking, heavy atom soaking etc).

The mentioned steps of crystal harvesting (crystal extraction) and processing require a significant amount of manpower and time, especially when large amounts of crystals needs to be tested or when large libraries of compound are assayed in the context of structure-guided design of bioactive molecules. Furthermore, due to the necessity of several manual steps the results of the analysis are dependent on the skills of the operator. Moreover, the samples, e.g. crystallized biological material, may be mechanically damaged by removing and displacing from the multi-cell plate.

SUMMARY OF THE INVENTION

Thus, there may be a need for a possibility to reduce an interaction of the operator with the samples of the biological material.

Those needs may be covered by the subject-matter of the independent claims. Further exemplary embodiments are evident from the dependent claims and the following description.

According to a first aspect of the present invention a multi-cell plate for automated incubation, processing, harvesting and analysis of samples of biological material is provided. The multi-cell plate comprises a body with a plurality of cells and a sealing film for sealing the cells on a first side of the body. Moreover, the multi-cell plate comprises a sample film for sealing the cells on a second side of the body. The sample film is adapted for accommodating a biological material for crystallization. Furthermore, the sample film comprises a material compatible with laser-induced photoablation.

In other words, the idea of the present invention according to the first aspect is based on providing a multi-cell plate with an ultrathin sample film consisting of a material whose thickness and composition make it directly compatible with crystal recovery by film excision, in particular with laser-induced photoablation and with sample analysis methods such as X-ray data collection. Moreover, the sample film is directly compatible with freezing techniques. The compatibility with laser ablation makes possible, on the one hand a cutting out of the film with sample by an automated laser, and allows to avoid the step of an operator extracting the crystal manually with a loop.

On the other hand, the compatibility of the sample film, made e.g. of polymer, with laser ablation allows for a hole to be made by a laser under the sample. The hole may be used for supplying chemicals like cryo protectants or ligands to the sample without the necessity to remove it from the multi-cell plate. Thus, again it allows to avoid the step of an operator manually removing the sample and transferring it to a solution containing the chemicals. Furthermore, the hole may be employed to remove excessive sample fluid also denoted as crystallization solution after crystallisation or chemical solution after incubation. In this way, background scattering during a data-collection is reduced and the results of an analysis are improved. Furthermore, because the amount of material is reduced, a cryo-freezing rate is increased. Thus, cryo-freezing could be applied directly, without addition of cryo-protectant.

Furthermore, the sample film material and thickness make it possible to offer an exceptional transparency and a low birefringence and allow to analyze the crystal with visible, ultraviolet light and with X-rays with minimal interference of the material. In this way, an in-plate-x-ray-data-collection is possible which reduces the interactions of an operator with the sample. The mentioned advantages allow an automation of the process of crystal harvesting, processing and analysis.

Thus, by employing a sample film compatible with x-ray data analysis and laser photoablation consisting of polymer material for the multi-cell plate several steps of incubation, processing, harvesting and analysis of samples may be automated and manual interaction with the samples may be avoided. Therein, automated or automatic may denote that no user interaction is required or alternatively user interaction is minimized. Furthermore, automation may also denote the replacing of manual interaction with the sample by remote operation of system components.

Further advantages of employing a sample film consisting of cyclic olefin copolymer material for the multi-cell plate are that it is compatible with post-processing steps such as cryo applications e.g. freezing. Moreover, the cyclic olefin copolymer has a relatively high moisture barrier as compared to other clear polymers. At the same time the olefin copolymer has a relatively low moisture absorption rate. These features may help in enhancing crystal formation and growth, and in particular allows long incubation time without alteration of the content of the cells.

The multi-cell plate may comprise a plurality of cells. For example, 24, 96 or 384 cells may be included in the body of the multi-cell plate. The body may comprise a material such as glass or plastics, e.g. cyclic olefin copolymer (COC) or polystyrene. Therein, the body may be injection molded.

A sealing film serves for sealing the cells on a first side of the body, e.g. on an upper part. The sealing film may be bounded or joined to the body e.g. by an adhesive or by thermo fusion. The sealing film may be transparent and e.g. comprise the same material as the sample film or a different material. If the sealing film is of the same material as the sample film then background is minimized and the quality of the signal is further improved.

The sample film may also be denoted as crystallization film and may be bonded or joined to the body on a second side, e.g. on a lower side of the body. The joining may also involve an adhesive and/or thermo fusion. The sample film may be arranged in parallel to the sealing film on the body. The sample film may be e.g. made only of one polymer, such as cyclic olefin copolymer, or alternatively comprise a combination of materials. Furthermore, the sample film may cover all of the plurality of cells. Alternatively, each cell may individually be covered by a separate sample film.

The sample film is adapted for accommodating a sample of biological material for crystallization. The biological material may be incubated onto the sample film. Therein, the biological material may for example include proteins or nucleic acids or other biological molecules. The incubation and crystallization may be done e.g. in the following ways: a certain amount of a material to be crystallized may be mixed with an amount of a crystallisation solution to form a crystallisation drop. The crystallisation solution decreases the solubility of the sample and encourages the formation of the crystalline material in the crystallization drop. In a vapour diffusion method for the formation of the crystalline material, the crystallization drop is left to equilibrate through a gas phase of a large volume of a precipitate liquid also present in a reservoir inside the cell.

In a batch and a micro-batch method for the formation of the crystalline material, the crystallisation drop is isolated from the gas phase. The isolation of the crystallisation drop from the gas phase is typically achieved using a liquid paraffin or an oil which is placed on the crystallisation drop on the sample film. The liquid paraffin or the oil does not allow an equilibrium against an excess of the precipitate liquid. Alternatively, a hanging drop method may be applied for crystallization. In this method the sample film with a drop of sample solution is oriented in such a way that it is located in the upper part of the body of the multi-cell plate. After crystallization, i.e. after crystal growth the samples may have sizes of a few millimeters to a micron or even less.

Mixing of the biological material and the crystallization solution on the sample film may take place while the sealing film is not on the multi-cell plate. After the mixing the sealing film may be joined to the plate. During or after crystallization the sample may be processed e.g. by e.g. supplying cryo protectants or ligands to the sample or by removing sample fluid surrounding the biological material. Furthermore, after crystallization the sample may be harvested or recovered together with the sample film or directly analyzed in the multi-cell plate. The analysis may include data collection e.g. by X-ray diffraction.

According to an exemplary embodiment of the invention the sample film comprises at least one of the following materials: a cyclic olefin copolymer material or a polyimide material. The use of COC may be particularly advantageous because for example at a thickness of 25 μm it offers an exceptional transparency and a low birefringence as compared to other clear polymers.

According to a further exemplary embodiment of the invention the sample film comprises a thickness between 1 μm and 50 μm. Particularly, the sample film comprises a thickness between 10 and 40 μm. Preferably, the sample film comprises a thickness between 20 and 30 μm. When using COC material a thickness of 25 μm may be advantageous. This ultra-thin dimensioning of the sample film provides for a good cutability by laser ablation and makes sure that the X-ray scattering caused by the sample film is minimized.

According to a further exemplary embodiment of the invention the sample film may comprise an anti-adhesive material. The anti-adhesive material may for example be a Silane compound (Silanization) or Polytetrafluoroethylene (PTFE) or obtained by plasma implantation of hydrophobic material like $SiO_2$. The employment of an anti-adhesive material may help in minimizing the interaction of the crystal sample film with the sample, e.g. with a crystal, located thereon.

According to a further exemplary embodiment of the invention the sealing film may be of the same material as the sample film. In this case background is minimized and the quality of the signal is further improved.

According to a further exemplary embodiment of the invention the body comprises a predetermined pattern of markers for allowing an automated and very accurate positioning, identification and/or localization of cells of the multi-cell plate and/or of the crystals contained in them. In other words, the markers provided on the multi-cell plate allow for example an identification unit or a control unit of an automated system to recognize a particular cell of the plurality of cells with a high precision of for example 5 microns. Therein, the predetermined pattern of markers may be stored e.g. in a memory of the control unit. Furthermore, the position of crystals may be precisely stored relative to the predetermined markers or patterns.

Furthermore, the markers may also help in localizing the position of the biological material in the identified cell. This significantly facilitates the automation of the process. Thus, based on the markers a system may automatically incubate in defined cells different biological material. Furthermore, based on the markers a system may save the location and identity of certain cells and/or of crystals. Moreover, a positioning device may position the multi-cell plate automatically in an analysis device for a certain sample to be examined based on the known position of the markers. In addition, based on the identification of the different cells a fluid unit may administer different amounts of fluid to different samples.

According to a further exemplary embodiment of the invention the markers are selected from the following group of markers: haptical markers such as recesses and protuberances or optical markers. Combinations of the different markers may be advantageous. The haptical markers may for example be designed as holes or pins located on the body of the multi-cell plate. The optical markers may for example be certain patterns or colors located on the surface of the body of the multi-cell plate or on the sample film. Therein, the haptical markers may also be used as holding and positioning elements, and the optical markers for positioning elements. For example, holders or grips of a robotic system may be inserted into markers designed as holes. In this way, the markers fulfill the functionality of positioning as well as the functionality of identification of certain cells and/or certain crystals. The locations of the cells and/or crystals with respect to the markers may be stored in a positioning system connected to the robotic system. Moreover the haptical markers defined as holes can be used as open areas in the frame of the plate to optically define the position of the pins for further precise positioning on the sample film.

According to a second aspect of the present invention an automated system for incubation, processing, harvesting and analysis of samples of biological material, e.g. crystals, is presented. The system comprises a multi-cell plate as described above and a cutting device also denoted as a film penetrating device. The cutting device may be used to penetrate the film, produce openings in it or excise sections of the film. In other words, the cutting device may be adapted for piercing the film. Particularly, the cutting device may be adapted for penetrating or locally piercing the sample film by photo ablation. Alternatively, the cutting device may be a mechanical cutting device such as e.g. a needle, a scalpel, etc.

In other words, an idea of the present invention according to the second aspect is, inter alia, based on providing an automated high-throughput system which includes a cutting device which is adapted for automatically interacting with the multi-cell plate thus helping in avoiding operator interactions with the samples. For example, the cutting device may be employed for automatically cutting the sample film around the sample for allowing a recovery of the sample. Additionally or alternatively the cutting device may be employed for providing holes or openings in the sample film, e.g. of varying shapes and sizes, for administering a fluid into the cell e.g. with a solution deliver unit or for extracting a fluid from the cell e.g. with a solution aspiration unit. Furthermore, the hole may function as a depressurization hole. Thus, manual interactions with the samples are avoided during incubation, processing, harvesting and analysis of the samples.

The automated system may additionally comprise a fluid unit for example including a solution aspiration unit and one or multiple solution delivery units. Moreover, the automated system may further comprise a positioning device for example including a sample mounting device. Furthermore, a cryo-cooling device, a device for storing multi-cell plates and a device for storing frozen crystals may be included in the automated system. The different additional devices are described in more detail below.

According to a further exemplary embodiment of the invention the automated system further comprises an identification device for automatically identifying a certain cell, e.g. a first cell, of the multi-cell plate based on markers on the plate and/or based on image analysis. Furthermore, the identification device may be adapted to identify the samples trough the automatic identification of the crystallization drops, within the identified cell. Furthermore, the identification device may be adapted to identify the samples, in particular the crystals, within the identified cell. Therein, identifying may include acquiring images of the cells by a microscope or by a camera and analyzing the images e.g. by a control device. After identification a certain cell may be positioned and orientated on a cell support of a fluid unit, of a cutting device or of an X-ray device in such a way that the respective device or unit may interact with the identified cell and its contents. The positioning may be executed by a positioning device.

Preferably, the identification of the samples by automatically identifying crystallization drops in the cells may be employed in different imaging systems of the automated system. For example, this automatic identification may be employed for crystallization incubators, for the harvesting system and for beamlines for in plate crystal analysis.

Therein, the positioning device may comprise a robotic arm and/or a plate support which is adjustable in three dimensions. Moreover, the positioning device may be connected to a control device on which information on the predetermined markers is stored. The control device may be functionally connected to the robotic arm and/or to the plate support.

According to a further exemplary embodiment of the invention the cutting device is designed as a nano second laser, a pico second laser or a femto second laser. The laser may advantageously be a short pulsed high energy laser adapted for photo ablation such that during cutting of the sample film a heat diffusion transfer is minimized. The laser may for example have a wavelength of 355 nm, 515 nm or 1030 nm. Alternatively, the cutting device may be designed as a mechanical cutting device such as a pin, a blade, a needle, a hollow needle, a scalpel and so on.

According to a further exemplary embodiment of the invention the automated system further comprises a fluid unit for supplying a fluid to a cell of the multi-cell plate and/or for extracting a fluid from a cell of the multi-cell plate. The cutting device is adapted to provide an opening such as a hole or a tunnel in the sample film.

Preferably, the opening is provided directly under the sample or in the direct vicinity of the sample within the identified and selected cell. The fluid unit, also denoted as crystal treatment unit, is connectable via the opening to the cell of the multi-cell plate.

The fluid unit may comprise a solution delivery unit which delivers chemicals to the crystals in the cells by depositing a drop or drops into or onto the hole. This puts into contact the crystallization solution containing the crystal and the solution containing the chemical delivered by the solution delivery unit so that the chemical may diffuse though the crystallization solution and reach the crystal. This process may be operated once or repeated sequentially to subject the samples to multiple treatments with different chemicals. For example treatment with a ligand could be followed by treatment with a cryo protecting agent.

Moreover, the fluid unit may comprise an aspiration unit for extracting a fluid from a cell of the multi-cell plate. The aspiration unit may remove the liquid surrounding the crystal in the cell of the multi-cell plate.

The fluid unit and particularly the solution delivery unit may be adapted for delivering volumes of a fluid ranging from 1 pl to 10 µl to the cell. Particularly, the fluid unit may be designed as a small volume dispensing system. In this way, the fluid unit may provide the sample automatically with the required amount and quality of fluid. Therein, the fluid may contain a solution with different chemicals. Particularly, different chemicals and different concentrations of chemicals may be supplied to the different cells of the multi-cell plate. In an alternative embodiment the fluid may be supplied directly to the sample film surface of an already harvested sample.

The fluid unit and the cutting device may be provided within a single machine or within two separate machines. For example, a harvester may be used to pierce an opening into a sample film. Subsequently, the multi cell plate may be moved to a different system for liquid delivery, e.g. to a standard pipetting robot or a specifically designed system. Alternatively, completely different systems may be used for piercing and delivering liquids and moving the plate to a harvester for a final crystal harvesting. In such example, it might be convenient to exert the opening for liquid delivery by a simpler method than laser cutting, such as e.g. by a sharp needle, i.e. by a mechanical system for piercing the sample film.

According to a further exemplary embodiment of the invention the cutting device is adapted to vary the dimensions and shapes of the opening depending on the amount of the fluid to be supplied to the cell or extracted from the cell. Therein, the cutting device may provide different sizes and shapes of holes on the same multi-cell plate. Furthermore, in a memory of a control device or on an information carrier an information on a certain amount of fluid to be administered may be stored for each cell of the multi-cell plate. The control device may be adapted to control the cutting device according to this information.

According to a further exemplary embodiment of the invention the cutting device is adapted to provide a small opening in a cell to equilibrate the pressure inside and outside a cell, before another operation occurs, e.g. before an opening on a sample to avoid the solution flowing outside the cell.

According to a further exemplary embodiment of the invention the fluid unit is adapted to supply at least one of a cryo protectant, a ligand solution or other agents like substrates, co-factors or phasing compounds to the cell. The ligand solution may comprise potential ligands used in the context of structure-guided design of inhibitors or other bioactive molecules.

According to a further exemplary embodiment of the invention the fluid unit, and in particular the aspiration unit, is adapted to apply a negative pressure, i.e. suction or vacuum, to a cell of the multi-cell plate. The negative pressure may be applied for extracting solution around the sample, e.g. around a crystal, to be harvested or analyzed. By removing excess solution at the sample, better X-ray diffraction results may be achieved because e.g. no change of position of the crystal may occur in this case. Furthermore, background scattering is reduced by removing the solution. Thus, in this way the signal over noise ratio may be improved. Therein, the opening is produced by the cutting device in such a way that it gives access to the solution in which the sample is located.

Moreover, by extracting the solution, the size of the sample is decreased, which facilitates cryo cooling because a faster transition to the cryogenic temperature is possible. In this way, also ice formation is prevented and the quality of the preservation of the sample is improved.

In other words, crystals may be prepared for x-ray diffraction experiments by removing the solution around them through gentle aspiration while the crystal remains on its original support, as opposed to the commonly applied method of extracting the crystal from the solution with some crystallization solution remaining around it. This simplifies the operation, reduces mechanical stress to the sample and allows full automation of the process.

According to a further exemplary embodiment of the invention the automated system further comprises a removing device for removing the harvested sample from the multi-cell plate and for mounting it into a support that facilitates manipulation and exposure of the sample to x-rays. The removing device may also be denoted as a sample mounting. The support may be a for example metallic pin. According to a further embodiment the removing device is adapted to apply negative pressure to the sample film and the pin is designed to be hollow so that negative pressure or vacuum can be applied through it to facilitate contact between the tip of the pin and the sample film. Furthermore, the cutting device is adapted to cut around a crystal on the sample film.

According to a further embodiment of the invention the removing device may comprise a system for adding an adhesive to the tip of the pin to ensure permanent attachment of the excised sample film to the pin. Therein, the removing device is adapted to bring the hollow pin in contact with the sample film and apply negative pressure to the sample film to ensure contact between the film, the pin and the adhesive.

According to a further exemplary embodiment of the invention the automated system further comprises or is associated with an analyzing device such as an X-ray device and an imaging device such as an X-ray detector. The analyzing device may be adapted for in-plate-data-collection or for analyzing single harvested samples.

According to a further exemplary embodiment of the invention the automated system further comprises a freezing unit also denoted as freezing station. The freezing unit is adapted to provide a cryogenic treatment to single harvested samples or to multi-cell plates.

According to a further exemplary embodiment of the invention the automated system further comprises a storage unit also denoted as storage station. The storage unit is adapted for storing single harvested samples and multi-cell plates before analysis and/or processing.

According to a third aspect of the present invention a method for operating the automated system described above is presented. The method comprises the following steps: identifying a cell of the multi-cell plate and/or one or more samples in the cell. Providing an opening in the sample film of the identified cell by the cutting device; connecting the fluid unit to the cell via the opening; supplying a fluid to the cell or extracting a fluid from the cell by the fluid unit. Furthermore, the method may comprise varying the dimensions e.g. the diameter and the orientation, of the opening depending on the amount of fluid to be extracted or supplied. This step may be executed before connecting the fluid unit to the cell. For example, the opening may be connected to a solution delivery unit of the fluid unit and chemicals may be delivered to the cells or directly to the crystals by diffusion via the opening. Alternatively, the opening may be connected to an aspiration unit of the fluid unit and sample solution may be extracted from the cell.

According to a further exemplary embodiment of the invention the identifying of the cell takes place automatically based on markers on the plate and/or based on image analysis by the positioning device. Identifying a cell may also include identifying the location and orientation of a cell, of several cells or of each cell of the multi-cell plate. Furthermore, the positioning device may indentify the location of the samples within the cells. Alternatively, the identification of the cell may be done directly by a user or by a user using a remote control unit.

According to a further exemplary embodiment of the invention a fluid may be supplied to the cell, the fluid being adapted for influencing a crystallization process of a crystal (or crystals) comprised within the cell. For example, a solvent may be introduced into the cell. This solvent may then partly or completely dissolve one or multiple small crystals comprised in the cell and the dissolved material may subsequently add to growing one or a few larger crystals with improved diffraction properties within the cell. The solvent may be e.g. water or solutions containing one or multiple crystallization reagents, like a pH buffer, salts, PEG, etc or other chemicals. Accordingly, crystal properties may be enhanced from multiple small crystals with poor diffraction properties to e.g. a single large crystal, or in general to crystals with improved diffraction properties.

Furthermore, the method may comprise several further steps. The order of execution and the number of the steps may vary. For example, the method may further comprise incubating a sample or a plurality of samples on the sample film of the multi-cell plate. Moreover, the method may comprise sealing the multi-cell plate with the sealing film. Furthermore, the method may comprise growing crystals e.g. by a vapour diffusion crystallization. These steps may be executed before providing an opening in the sample film.

Moreover, the method may comprise processing or post processing the samples after crystal growth. The processing may include e.g. supplying fluids with chemicals to the identified cell. Further steps may also comprise for example harvesting the sample film together with the sample from the multi-cell plate by cutting the sample film around the sample with the cutting device. After this the sample may be analyzed. Alternatively, the samples may be directly analyzed in the multi-cell plate e.g. by X-rays. Before analyzing, the harvested samples may be frozen in a freezing unit and stored in a storing unit.

According to a forth aspect of the invention a computer program element is provided which is adapted, when executed on a computer, to execute the method described above. This computer program element may for example be stored and executed on the control device of the system described above or executed from a remote location. This computer program allows the operator to record the position of crystals and specify the actions to be performed on them. These actions will be either directly executed, or recorded and executed at a later time in the robotic system. For example the positions of the recorded crystals can be used to automatically extract them from the multi-cell plates. Alternatively, the operator may decide on the shapes and numbers of sample film areas that will be excised to extract crystals from the cells of the multi-cell plate, and decide whether the solution delivery unit is used or not and which solutions to deliver. Furthermore, the operator may decide whether the solution aspiration unit will be used or not to remove the excess crystallization solution, whether crystals will be frozen or not in the cryogenic unit and whether they will be stored. The position of the crystals may also be used to determine the areas to be directly exposed to x-rays inside the multi-cell plate. The system and the software will allow individual identification of each of the crystals or group of crystals in the same cell.

According to a fifth aspect of the invention a computer readable medium is provided on which the computer program element described above is stored. In another aspect, the software accessible through the internet and operation of the system is operated in a remote controlled manner.

Furthermore, it should be noted that features described in connection with the different devices and methods may be combined with each other. These and other aspects of the invention will be apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
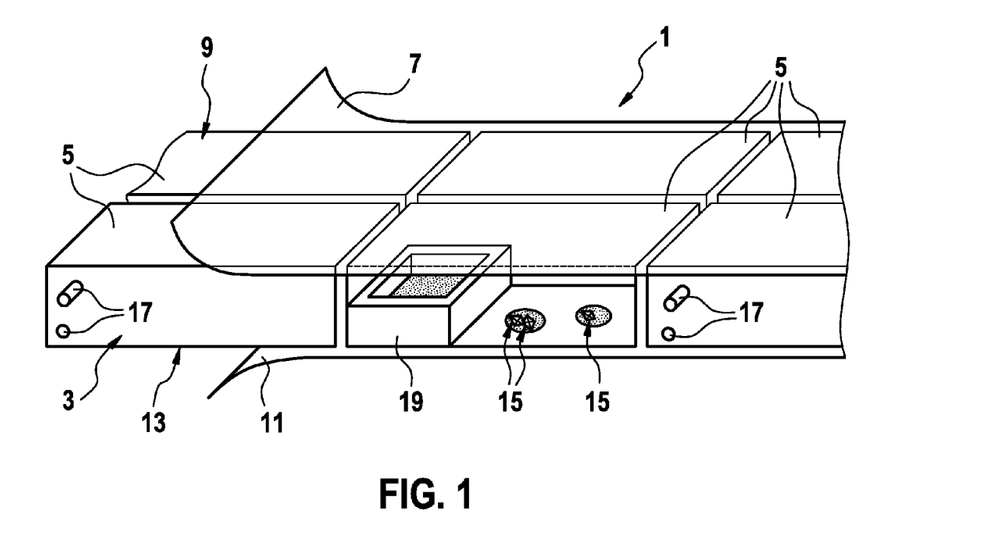
FIG. 1 shows a perspective view of a multi-cell plate according to an embodiment of the invention

In FIG. 1 a multi-cell plate 1 is shown in a perspective view. The multi-cell plate 1 is shown in a sitting drop application in which a sample 15 of biological material is incubated on a sample film 11 and the multi-cell plate 1 is oriented in such a way that during crystal growth the sample film 11 is located in the lower part of the multi-cell plate 1. Alternatively, the multi-cell plate 1 may be used in a hanging drop application (not shown in the Figures). In the hanging drop application the multi-cell plate 1 is oriented in such a way that the sample 15 and thus the sample film 11 is located in the upper part of the multi-cell plate 1, i.e. above the sealing film 7.

The multi-cell plate 1 comprises a body 3 with a plurality of cells 5. In the example shown, in each of the cells 5 a precipitate reservoir 19 with a precipitate liquid is located. The precipitate liquid induces a formation of crystals from the sample drop on the sample film 11 by vapor diffusion. The cells 5 are sealed by a sealing film 7 on a first side 9 of the body 3. Furthermore, on the opposing second side 13 of the body 3 the cells 5 are sealed by a sample film 11. The cells may be sealed airtight by the sealing film 7 and by the sample film 11.

The sample film 11 is made of a material compatible with photo ablation. Preferably, the sample film 11 is made of a cyclic olefin copolymer. Furthermore, the sample film 11 may include further polymers such as polyimide. Moreover, the sample film 11 is preferably cutable by laser ablation. The sample film 11 may be coated with a material, such as black carbon, which aids the cutting of the sample film 11. Furthermore, the sample film 30 preferably has a thickness between 1 and 50 µm.

The material and the thickness of the sample film 11 are designed to provide a minimum of X-Ray scattering during an analysis of the sample 15. In addition, the sample film 11 may be coated with an anti-adhesion material such as PTFE for preventing the sample from adhering to the sample film 11. Furthermore, the sample film 11 may be inert to the sample 15, to the sample solution and to the precipitate liquid.

By employing a sample film 11 consisting of cyclic olefin copolymer for the multi-cell plate 1 several steps of processing, harvesting and analysis of samples 15 may be automated and manual interaction with the samples may be avoided. This is due to the properties of the cyclic olefin copolymer material such a compatibility with photo ablation which allows an automation of a harvesting process. Furthermore, the cyclic olefin copolymer allows a small opening to be made in the film by laser ablation. The opening may be used for automatically supplying cryo protectants or ligands to the sample or for removing the sample solution as described below. Moreover, the high transparency and low birefringence of the cyclic olefin copolymer allow an in-plate-data-collection which reduces operator interactions with the sample.

Furthermore, for reducing user interactions the multi-cell plate 1 comprises markers 17 designed e.g. as holes, pins, recesses and optical patterns. The markers 17 are preferably arranged at the body 3 of the multi-cell plate 1 and may be used as holding devices for a robotic arm or for a positioning unit such as a plate support. Based on the locations of the markers the orientation and location of certain cells 5, and particularly, the orientation and location of samples 15, i.e. crystals, in the cells 5 of the multi-cell plate may be determined thus providing further automation of the incubation, processing, harvesting and analyzing of the samples.

Figure 2:
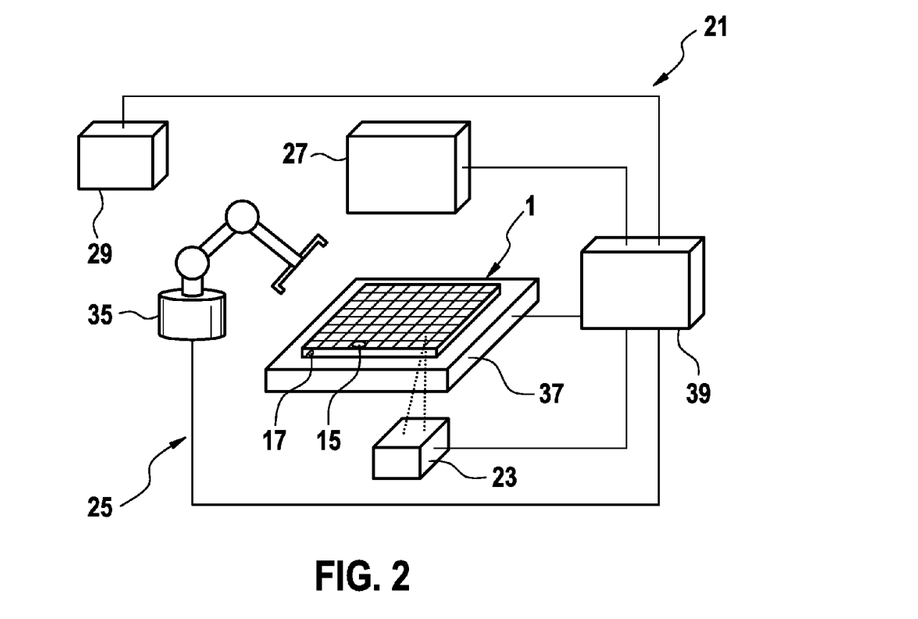
FIG. 2 shows a schematic representation of an automated system for incubation, processing, harvesting and analysis of samples of biological material according to a further embodiment of the invention

In FIG. 2 a schematic view of an automated system 21 for incubation, processing, harvesting and analysis of samples 15 of biological material is presented. The functionality of the system is explained in greater detail with respect to FIGS. 4 to 6.

The automated system 21 comprises a cutting device 23 designed as a mechanical cutter or preferably as a femtosecond laser. The cutting device 23 may include a scanning optic device e.g. for focusing and directing the beam of the laser onto a selected cell 5. Moreover, the system 21 comprises a positioning device 25. The positioning device 25 may comprise a robotic arm 35 e.g. for transferring the multi-cell plate 1 between different units of the system 21. Furthermore, the positioning device 25 may comprise one or several plate supports 37. The plate support may be e.g. an X-Y-platform movable by drives for positioning and orientating the multi-cell plate 1 within one of the units of the system 21. The positioning device 25 may be employed for receiving the multi-cell plate 1 and for aligning the plurality of cells 5 for rapid and automatic identification of the cells 5 e.g. initially by using the information on the geometry of the plate and more precisely by an identification device 27 and for automatically aligning the crystals under the working area of the laser. For this purpose, crystal positions recorded relative to the reference markers 17 may be used.

Moreover, the system 21 may comprise an identification device 27 for automatically identifying a cell 5 of the multi-cell plate 1 based on markers 17 on the multi-cell plate 1 and/or based on image analysis. The identification device 27 may comprise a microscope or a camera and may be connected to a control device 39 on which the predetermined positions of the markers 17 or an image analysis program are stored.

The automated system 21 may further comprise a fluid unit 29 for supplying a fluid to a cell 5 of the multi-cell plate 1 and/or for extracting a fluid from a cell 5 of the multi-cell plate 1. Therein, the fluid unit 29 may be divided into a solution delivery unit for supplying chemicals to the samples 15 and into an aspiration unit for withdrawing fluid from the cells 5. The fluid unit 29 as well as the cutting device 23 and the positioning device 25 are connected to the control device 39.

The control device 39 is adapted to initiate a cutting of a hole by the cutting device 23 in the sample film 11 of the multi-cell plate 1. Furthermore, the fluid unit 29 is connectable via the opening to a selected cell 5 of the multi-cell plate 1. The operation of the automated system 21 is described in detail below.

Figure 3:
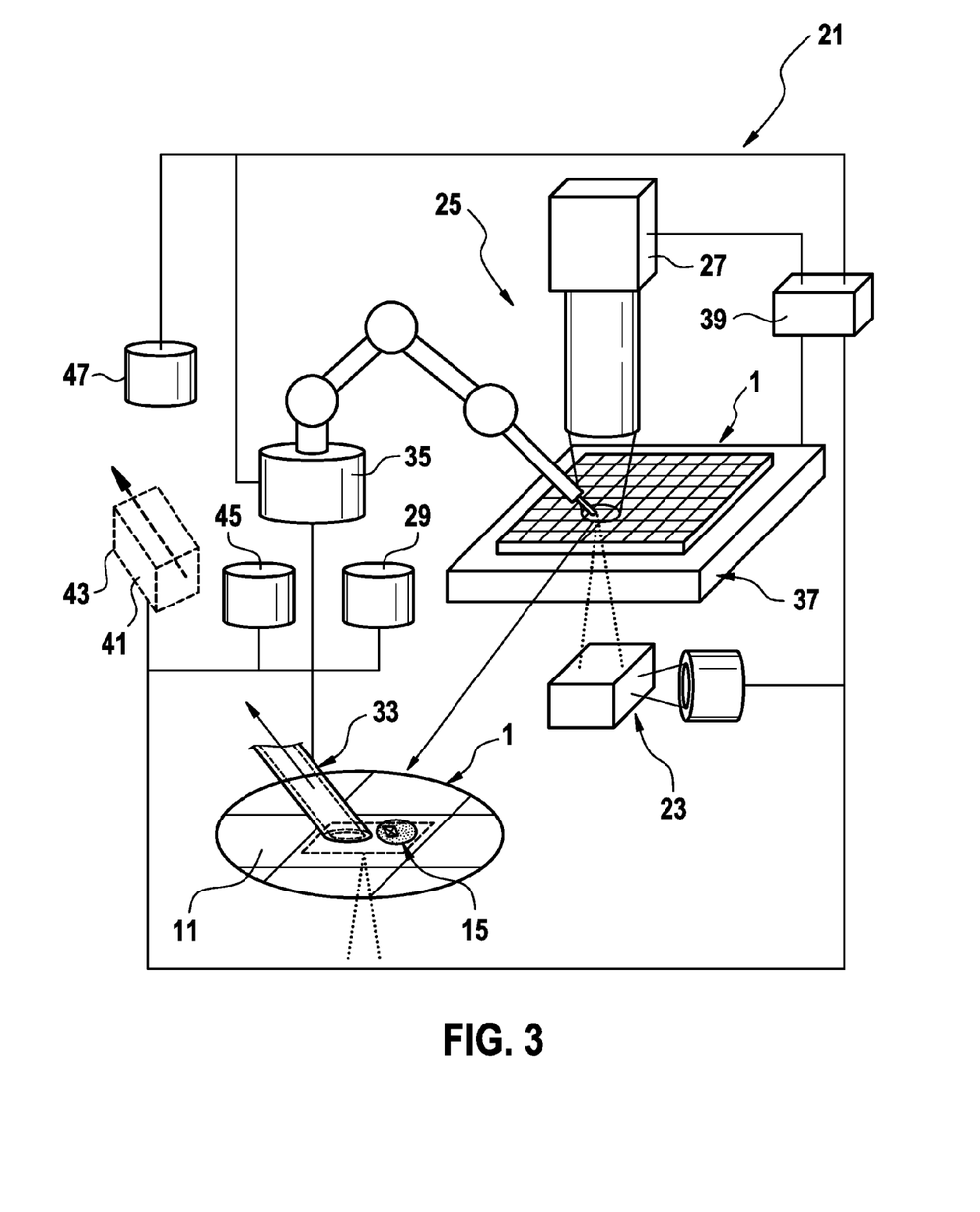
FIG. 3 shows a shows a schematic representation of an automated system according to a further embodiment of the invention

As shown in a further example in FIG. 3 the automated system may comprise further units and devices e.g. also connected to the control device 39. For example, the system 21 further comprises a removing device 33 also denoted as harvesting device. The removing device 33 may be designed as a hollow pin and may be adapted for applying negative pressure to the sample film 11 of the multi-cell plate 1. For this purpose the removing device 33 may be connected to the fluid unit 29. Therein, the removing device 33 may remove a sample 15 together with a part of the sample film 11 after the cutting device 23 cuts around the sample 15. The removing device 33 may be movable by the robotic arm 35.

Figure 8:
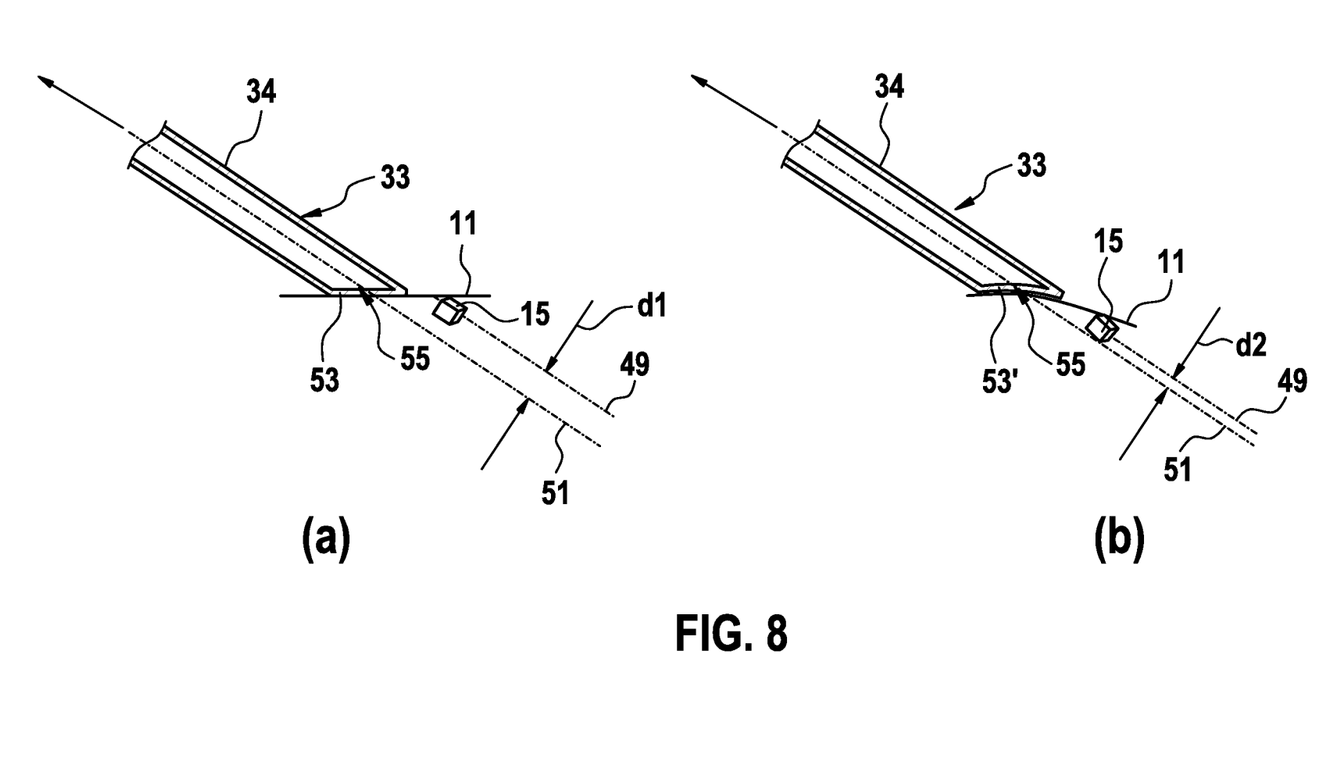

FIGS. 8(a) and (b) show examples of removing devices 33 provided as hollow pins 34. In FIG. 8(a), the removing device 33 comprises a beveled tip with a plane slanted surface 53 adjacent to an end opening 55 of the pin 34. This surface 53 may be placed on top of a sample film 11 having samples 15 on its opposite surface. By applying a weak vacuum to the hollow pin 34, the sample film 11 may be sucked and stick to the pin 34 such that using the removing device 33 the sample film 11 and the samples 15 sticking thereto may be handled and e.g. transported for subsequent analysis.

In FIG. 8(b) an alternative example of a removing device 33 is shown. In this example, the slanted surface 53' comprises a concave geometry. By pushing the pin 34 onto a flexible sample film 11 the latter may be slightly deformed and may sealingly abut to the end opening 55. By applying a weak vacuum to the hollow pin 34, the sample film 11 may be sucked and stick to the pin 34 such that using the removing device 33 the sample film 11 and the samples 15 sticking thereto may be handled. In such example, the sample film 11 will be slightly bent due to the concave form of the surface 53' of the pin 34. Due to such bending, the sample 15 sticking to the sample film 11 may come closer to a middle axis 51 of the pin 34, i.e. a distance d2 between the sample 15 and the middle axis 51 may become smaller than the respective distance d1 in the example shown in FIG. 8(a).

Moreover, the automated system 21 as shown in FIG. 3 further comprises an analyzing device 41 such as an X-ray device and an imaging device 43 such as an X-ray detector for data collection. These devices 41, 43 may be adapted for in-plate-data-collection, particularly when both the sample film 11 and the sealing film 7 of the multi-cell plate 1 are designed to be compatible with X-ray data collection. Furthermore, devices 41, 43 may be adapted for analyzing single harvested samples 15.

The automated system 21 further comprises a freezing unit 45 also denoted as freezing station. The freezing unit provides a cryogenic treatment to single samples 15. Furthermore, it is also possible to treat a multi-cell plate 1 in the freezing unit 45. However, for in-plate-data-collection the multi-cell plates 1 may be preferably transferred to directly to the analyzing device 41 without freezing.

Furthermore, the automated system 21 further comprises a storage unit 47 also denoted as storage station. In the storage unit 47 single harvested samples 15 and multi-cell plates 1 may be stored before analysis.

Figure 4:
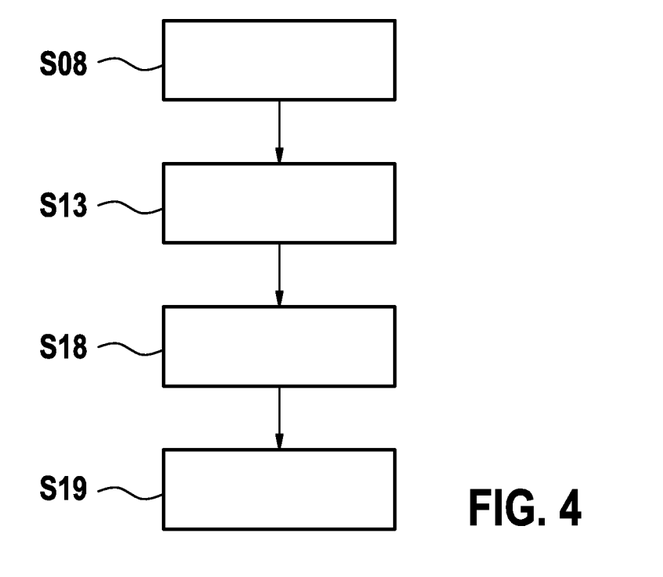
FIG. 4 shows a flow diagram of a method for processing the multi-cell plate according to embodiment of the invention

In FIG. 4 a method for post processing or processing the samples 15 directly in the multi-cell plate 1 is described. In particular, in FIG. 4 a method for supplying a fluid to the samples 15 is described. The fluid may contain chemicals such as possible ligands or cryo protectants. This method may be executed with the automated system shown in FIG. 2 or FIG. 3.

After a crystallisation of the biological material takes place in the cells 5 of the multi-cell plate 1, at least the position of one crystal 15 within one cell 5 is identified/registered in step S08 by the identification device 27 of the automated system 21. The identification may take place automatically e.g. based on markers 17 or on image analysis by a control device 39. Alternatively, a user may identify a cell and the position of the crystals within the cell 5 based on images provided by the identification device 27. This later step can also be performed remotely, for example through a web-based software interface.

Figure 6:
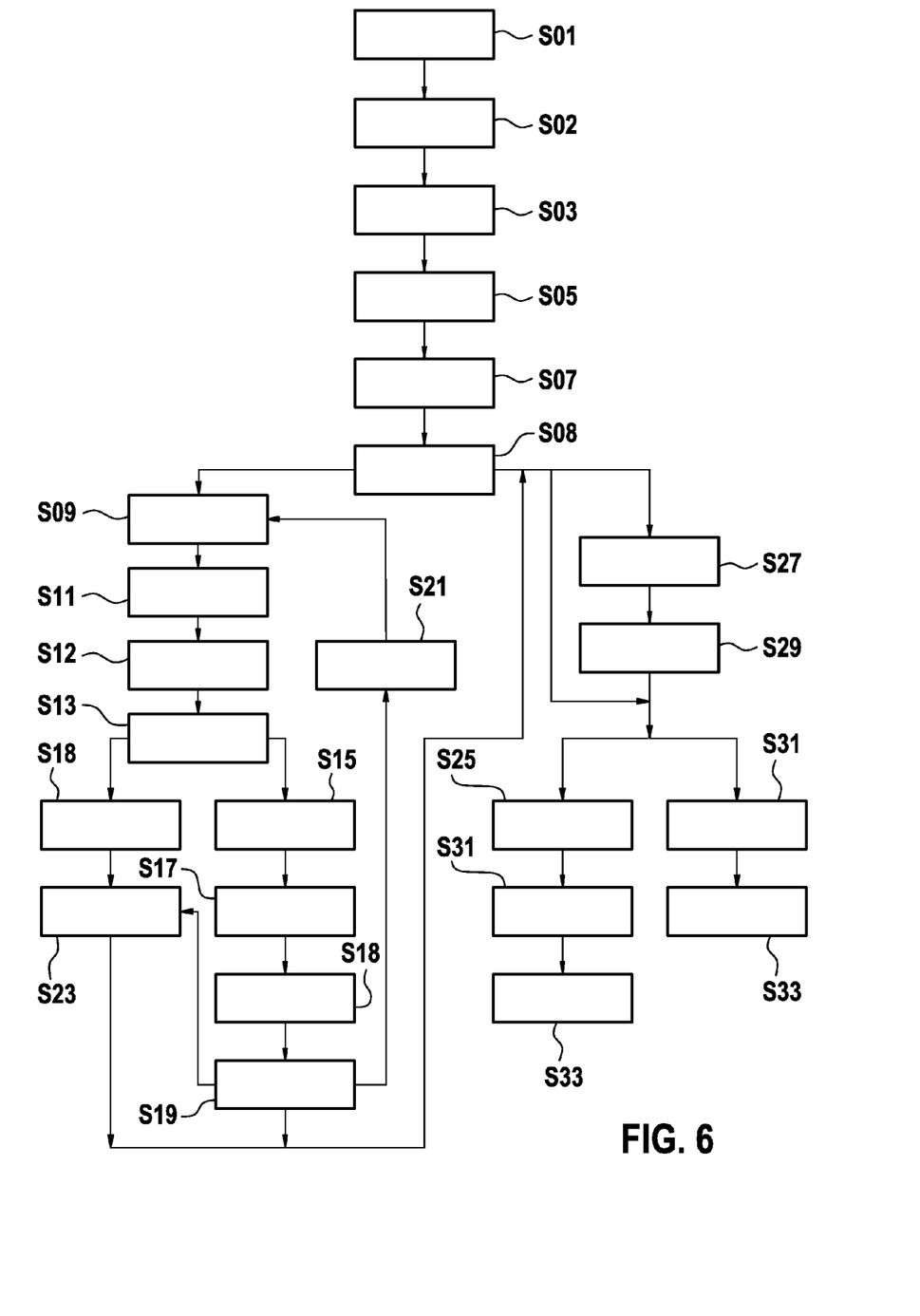
FIG. 6 shows a flow diagram of a method for automated incubation, processing, harvesting and analysis of samples of biological material according to an embodiment of the invention

In step S12 a depressurization opening could be provided in the sample film 11. In step S13 an opening is provided in the sample film 11 by the cutting device 23 e.g. by photo ablation. In step S18 the fluid unit 29 is connected to the opening. This may e.g. take place by displacing the multi-cell plate 1 to the fluid unit 29. Furthermore, in a step S19 a fluid in a selected amount and composition is supplied at the opening by the fluid unit 29. Then, the solutions may be aspirated through the opening to remove excess liquid. Then, the film area may be cut and the film may be mounted on or attached to the pin by the removing device 33. Then, the crystal may be frozen. Then, the crystal may be stored or directly exposed to x-rays. As shown in FIG. 6 further steps may be included in this method.

This method may be particularly advantageously applied in macromolecular crystallography which often requires treatment of crystals with chemicals. According to known systems and methods this treatment may be a manual and time consuming process requiring skilled operators. The method and the corresponding system 21 of the invention allow full automation of the process of delivering chemicals to crystals. The system 21 and also the method described allow crystals grown on the sample film 11 inside a closed cell 5 to be put in contact with the chemical through a small opening made in the sample film 11. Samples 15 and in particular crystals treated in this way may be directly exposed to x-rays in its original support, i.e. in the multi-cell plate 1. Alternatively, they may be recovered and exposed to x-rays after cryo-cooling for structural analysis.

Figure 5:
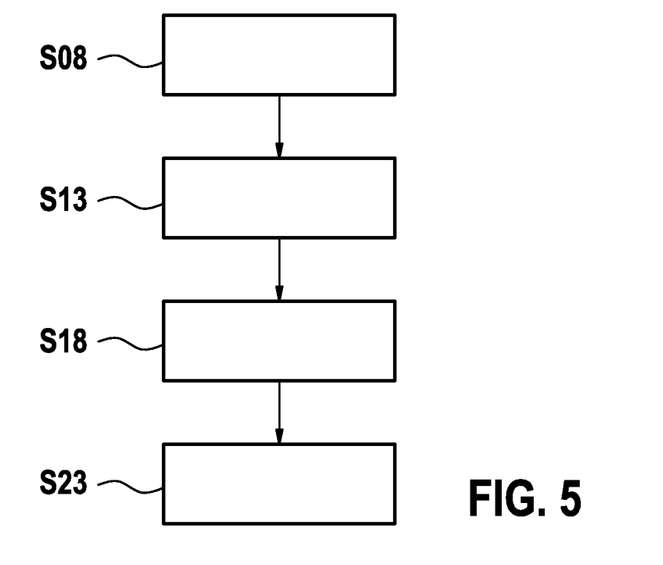
FIG. 5 shows a flow diagram of a method for processing the multi-cell plate according to a further embodiment of the invention

In FIG. 5 a further method for processing the samples 15 directly in the multi-cell plate 1 is described. In particular, the method in FIG. 5 is a method for extracting a fluid from the samples 15. The methods shown in FIG. 4 and FIG. 5 may be combined as described in FIG. 6.

The first steps S08, S13 and S18 of the method shown in FIG. 5 may be similar to the steps shown in FIG. 4. However, instead of adding a fluid with chemicals to the cell 5 a fluid is extracted e.g. aspirated from the identified cell 5 by the fluid unit 29. The opening provided in step S13 gives access to the solution in which the sample 15 and in particular the crystal is located. During this process the sample 15 remains in its original support, i.e. in the multi-cell plate 1 and the user interaction is minimized because the crystal does not have to be extracted from the multi-cell plate 1. The crystal may then be directly exposed to x-rays in its original support. Alternatively, the crystal may be recovered by excising the sample film area containing the crystal and presented to a cryo stream or to other cryogenic systems.

FIG. 6 shows a flow diagram of a method which combines several automated steps. Some of the steps shown in FIG. 6 may optionally require user interaction. Moreover, several steps of the method in FIG. 6 are executed only optionally. The steps described in connection with FIG. 4 and FIG. 5 are also included in the method shown in FIG. 6.

In a first step S01 biological material 15 is set on a sample film 11 of a multi-cell plate 1. In a second step S02 the cells 5 of the multi-cell plate 1 are sealed by a sealing film 7. In step S03 crystals are grown in the cells 5 e.g. by vapour diffusion crystallization. In step S05 images of the cells 5 of the multi-cell plate 1 are recorded by the identifying device 27 of the system 21. Images can also be taken in an imaging device external to the system and the images may be imported into the system through the software component. Therein, images of all the cells 5 may be acquired. Alternatively, only images of certain areas of the multi-cell plate 1 and thus only images of certain cells 5 may be acquired.

Figure 7:
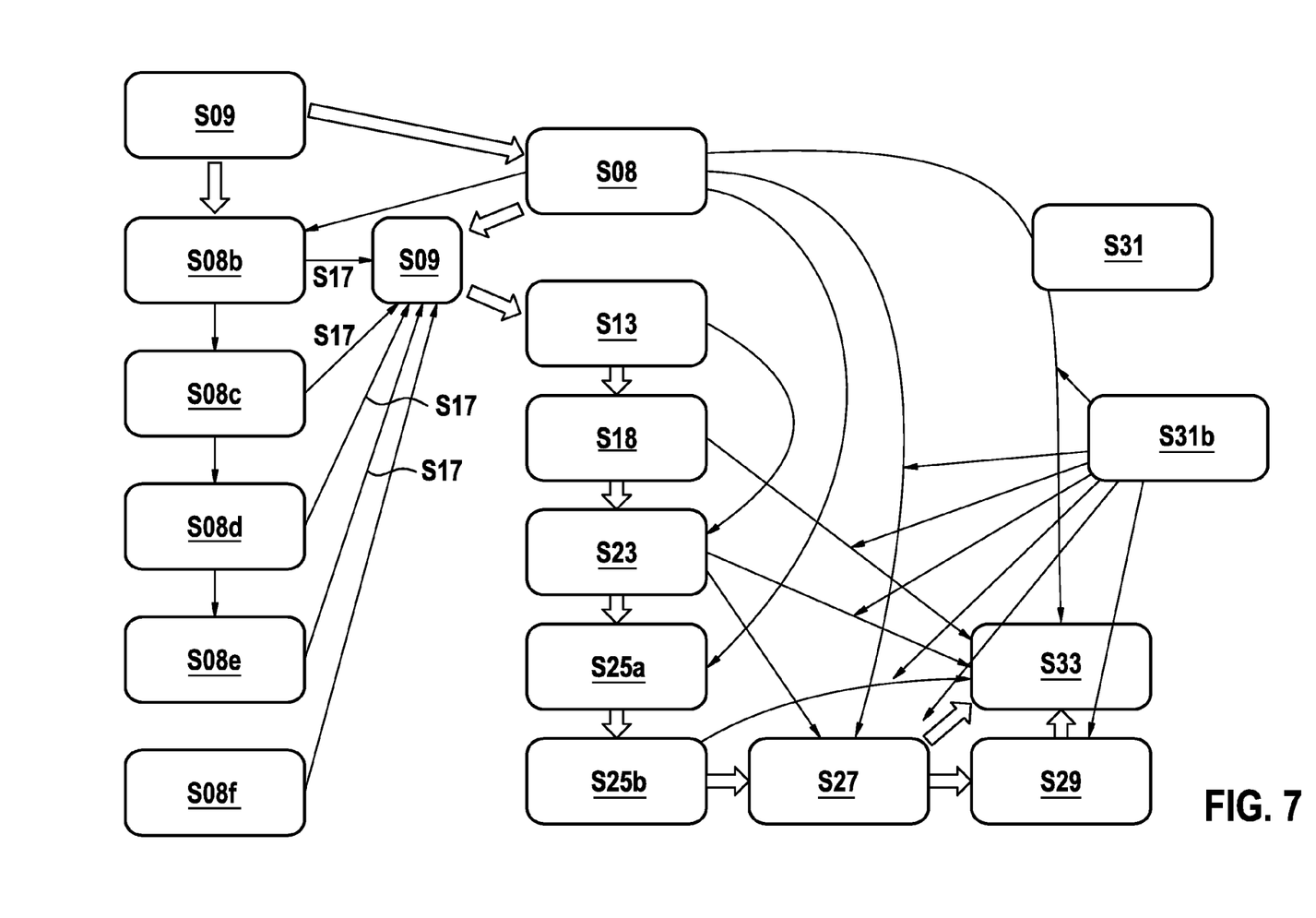
FIG. 7 shows part of a flow diagram of a method for automated incubation, processing, harvesting and analysis of samples of biological material according to a further embodiment of the invention FIG. 8a/b show examples of a removing device applicable for a multi cell plate according to an embodiment of the invention

In step S07 the images are taken by the control unit 39 of the system 21 and/or by an operator. The control unit 39 or the operator identifies in step S08 locations of one or multiple crystals in a cell 5. Preferably, steps S07 and S08 can be performed through an external system and recorded positions and images may be provided to the control unit of the system. In case of the identification by the control unit 39 this step may be conducted automatically. e.g. based on markers 17 or on image analysis. After the identification in step S08 an operator or the control unit 27 may select how to process the samples 15 of the multi-plate and which samples 15 are to be processed. These operations may include steps S08b to S08f which are shown in FIG. 7 and which may be executed e.g. after identifying the positions of the crystals in step S08 and before transferring the multi-cell plate 1 in step S09. Alternatively, steps S08b to S08f may be performed after transferring the multi-cell plate 1 in step S09 by a positioning device. Therein, these steps may include specifying a cutting area (S08b) specifying a chemical treatment and which solutions and which volumes are to be used for this treatment (S08c). Furthermore, specifying a position to make an opening (S08d) and specifying whether liquid is to be aspirated (S08e). Moreover, specifying whether crystals are to be analyzed in plates or harvested with the laser and mounted on a pin and whether they are going to be frozen or analyzed without freezing (S08f). At least steps S07, S08 and S08b to S08f may be performed remotely for example through an internet-based software or may be performed earlier and recorded so that all operations are performed at a later time in the system.

As shown in FIG. 6 after the crystal growth the multi-cell plate 1 may be transferred to the system (S09) and operations S08 to S08f executed through the software component of the system. Alternatively, steps S08 to S08f may be introduced (either through the system software or through other software for example a web-based software for remote operation) and recorded. At a later point this information is transferred to the system (S17) and the multi-cell plate is placed in the system (S09) so that the processing may start.

Once the plate is in the system and according to the protocol selected through steps S08 to S08f the sample 11 may be processed in different ways. For example, the plate is placed in the system and the crystal is aligned into the working area (S09), then an opening is made (S13), then solution is aspirated (S23), then the sample may be harvested by a removing device 33 in step S25. For this purpose the film area around the crystal is excised with the laser system (S25a), then the film area containing the crystal is mounted on a pin (S25b) and the harvested crystal is either frozen (S27) in the freezing unit or analyzed directly in the X-ray analysis system (S33). Therein, steps S25a and steps S25b are not shown in the Figures. To perform step S33 precise crystal positions are transferred from the system to the x-ray analysis device in step S31b (not shown in the Figures). If the harvested crystals (S09, S13, S13, S15b, S25a) are frozen (S27) in the freezing unit they may be either analyzed directly with X-rays (S31b, S33), or stored (S29) in the storage unit and analyzed later (S31b, S33).

Multiple variations to this protocol are possible, as indicated in FIG. 7. For example, after making an opening, chemicals may be delivered to crystals (S18) with the solution delivery unit of the fluid unit, then liquids may be aspirated (S23) and the process proceed like shown in FIG. 6 and described above. Solution delivery in step S18 and aspiration in step S23 may be repeated any number of times, for example to deliver multiple solutions of the same or different compositions sequentially before proceeding to steps S25 and further.

In another example, crystals can be harvested without any treatment. This would involve S09, S25a, S25b, S27 (optionally), S29 (optionally) and S33 (optionally, also including (S31b) in this case). In another example, crystals may be directly analyzed in the multi-cell plates. This involves identification of the crytal positions (S08), transfer of the crystal positions relative to the markers 17 to an x-ray analysis device (S31b) and transfer of multi-cell plates to x-ray analysis device and analysis by X-rays (S31). The results of the in-plate-data collection are enhanced by the use of a sample film 11 as described above. It is also possible to remove the liquid without removing the crystal and analyse the crystal inside the plate (S08, S09, S13, S18, S31b, S31). Other possible crystal processing and analysis protocols are indicated in FIG. 7.

In more detail, with reference to FIG. 6 again, after the crystal growth the multi-cell plate 1 may be transferred to a freezing unit 45 and frozen, i.e. cryo processed in step S27. Furthermore, the multi-cell plate 1 may be transferred to a storage unit 47 and stored in step S29. These steps are optional. After cryo treatment and storage or instead of these steps the multi-cell plate 1 may be transferred directly to an analyzing device 41 such as an X-ray device in step S31. In this case, in-plate-data collection takes place by an imaging device 43 in step S33. For example, the sample 15 of a certain cell 5 is analyzed by X-ray diffraction.

Alternatively, a selected sample 15 may be harvested by a removing device 33 in step S25 before analysis. In a further alternative (not shown in the Figures) the sample 15 may be harvested before freezing S27 and before storing S29. For harvesting the multi-cell plate 1 may be brought into position by a positioning plate 37 e.g. above a cutting device 23. Therein, the removing device 33 may be designed as a hollow pin as shown in FIG. 3. While the cutting device 23 cuts the sample film 11 around the selected sample 15 a negative pressure is applied to the sample film 11 below the sample 15. In addition to the negative pressure an adhesive e.g. a glue may be applied at the tip of the removing device 33 for ensuring a secure attachment of the sample 15 to the removing device 33. After harvesting the sample 15 may be stored, frozen and/or analyzed.

After crystal growth and before the steps S25 to S33 the samples 15 may be processed in their original support, i.e. in the multi-cell plate 1. In step S09 the multi-cell plate 1 may be transferred by the positioning device 25 to different units and devices of the system 21. For example, the positioning device 25 may bring the multi-cell plate 1 into correct position and orientation above the cutting device 23 or transfer the multi-cell plate 1 to the fluid unit 29. Furthermore, steps similar to the steps described in relation to FIG. 4 and FIG. 5 may follow step S09.

In step S11 a position, shape and size of an opening to be provided by the cutting device 23 at an identified cell 5 is selected. The selection may take place automatically be the control device 39 or by an operator. In step S13 the opening in the sample film 11 is provided by the cutting device 23 e.g. below the sample 25. Through the opening chemicals may be administered to the sample 15. Furthermore, a fluid such as the sample solution may be extracted through the opening. In step S15 the composition of the fluid to be supplied to the a certain cell 5 is selected. In step S17 the selected information is transferred to the fluid unit 29. Furthermore, in step S18 the fluid unit 29 is connected to the opening and a fluid in a selected amount and composition is supplied at the opening by the fluid unit 29 in step S19. This process, i.e. steps S09 to S19 may be repeated in step S21 with different chemicals such as different potential ligands and finally with a cryo protectant.

Alternatively, after providing the opening in the sample film 11 in step S13 a fluid may be extracted from the cell 5 by applying suction via the fluid unit 29 in step S23 as explained in FIG. 5. As shown in FIG. 6 step S23 may optionally be executed after chemicals are supplied to the sample 15 in step S19. Subsequently to supplying fluids to the cell 5 and/or extracting fluids from the cell 5 steps S25 to S33 may be executed.

It has to be noted that embodiments of the invention are described with reference to different subject matters. In particular, some embodiments are described with reference to method type claims whereas other embodiments are described with reference to the device or system type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

Furthermore, the term "comprising" does not exclude other elements or steps, and the indefinite article "a" or "an" does not exclude a plurality. The mere fact that certain measures are re-cited in mutually different dependent claims does not indicate that a combination of these measures cannot be used to advantage. Any reference signs in the claims should not be construed as limiting the scope.

LIST OF REFERENCE SIGNS 1 multi-cell plate
3 body
5 cell
7 sealing film
9 first side of body
11 sample film
13 second side of body
15 sample/biological material for crystallization
17 marker
19 precipitate reservoir
21 automated system
23 cutting device
25 positioning device
27 identification device
29 fluid unit
31 fluid with chemicals
33 removing device/mounting unit
34 pin
35 robotic arm
37 plate support
39 control device
41 analyzing device
43 imaging device
45 freezing unit
47 storage unit
49 axis through sample
51 middle axis of pin
S01 Incubating biological material on a sample film of a multi-cell plate
S02 Sealing the cells of the multi-cell plate by a sealing film
S03 Growing crystals
S05 Recording images of the cells of the multi-cell plate by the identification device
S07 Providing the images to a control unit and/or to an operator
S08 Identifying positions of crystals in a cell e.g. based on markers or on image analysis by the identification device
S08b Specifying an area to be cut by the cutting device, particularly by a laser
S08c Specifying whether chemicals are to be delivered (with the solution delivery unit), which ones, and in which quantities
S08d Specifying a position of the opening
S08e Specifying whether liquid is to be aspirated
S08f Specifying whether crystals are to be analyzed in plates or harvested with the laser and mounted on a pin and whether they are going to be frozen or analyzed without freezing
S09 Transferring the multi-cell plate by a positioning device
S11 Selecting a position, shape and size of the opening to be provided by the cutting device at a first cell (if not already done in S08d)
S12 providing a depressurization opening in the sample film
S13 Providing the opening in the sample film by the cutting device
S15 Selecting the composition of the fluid to be supplied to the first cell (if not already done in S08c)
S17 Transmitting the selected information to the system
S18 Connecting the fluid unit to the opening
S19 Supplying a fluid in a selected amount and composition at the opening by the fluid unit
S21 Repeating steps S09 to S19
S23 Extracting fluid from the cell by applying suction via the aspiration unit of the fluid unit
S25 Harvesting the sample by a removing device
S25a Cutting a sample film area around a crystal or around a group of crystals
S25b Mounting the film area onto a pin with the removing device
S27 Transferring the multi-cell plate or the mounted crystal to a freezing unit and freezing
S29 Transferring the multi-cell plate or the mounted crystal to a storing unit and storing
S31 Transferring the multi-cell plate to an analysis device
S31b Transferring crystal positions to an x-ray analysis device
S33 Data collection/Analyzing the sample by an imaging device

The invention claimed is:

1. Multi-cell plate for automated incubation, processing harvesting and analysis of samples of biological material, the multi-cell plate comprising
a body with a plurality of cells;
a sealing film for sealing the cells on a first side of the body;
a sample film for sealing the cells on a second side of the body
and for accommodating a biological material for crystallization;
wherein the sample film comprises a cyclic olefin copolymer material and comprises a thickness between 1 μm and 50 μm.

2. Multi-cell plate according to claim 1, wherein the sample film comprises an anti-adhesive material.

3. Multi-cell plate according to claim 1,
wherein the body comprises a predetermined pattern of markers,
wherein the markers are selected from the following group of markers: recess, protuberance and optical marker.

4. Automated system for incubation, processing, harvesting and analysis of samples of biological material, the system comprising
a multi-cell plate according to claim 1;
a cutting device for
penetrating the sample film.

5. Automated system according to claim 4, wherein the cutting device penetrates the sample film by photo ablation.

6. Automated system according to claim 4, further comprising
an identification device for automatically identifying a cell and/or a position of a crystal in a cell of the multi-cell plate based on markers on the multi-cell plate and/or based on image analysis.

7. Automated system according to claim 4, wherein the cutting device is one of a nano second laser, a pico second laser and a femto second laser.

8. Automated system according to claim 4, further comprising a fluid unit for supplying a fluid to a cell and/or to a crystal in the cell of the multi-cell plate and/or for extracting a fluid from a cell of the multi-cell plate;

wherein the cutting device provides an opening in the sample film;

wherein the fluid unit is connectable via the opening to the cell of the multi-cell plate.

9. Automated system according to claim 8, wherein the cutting device varies the dimensions and/or shape of the opening automatically depending on the amount of the fluid to be supplied or extracted.

10. Automated system according to claim 8, wherein the fluid unit supplies at least one of a cryo protectant and a ligand solution to a cell of the multi-cell plate.

11. Automated system according to claim 8, wherein the fluid unit applies a negative pressure to a cell of the multi-cell plate.

12. Automated system according to claim 4, further comprising a removing device for removing the sample from the multi-cell plate by applying negative pressure to the sample film;

wherein the cutting device cuts around a sample on the sample film.

13. Method for operating the automated system according to claim 4, the method comprising the following steps identifying a cell and/or a position of crystals in a cell of the multi-cell plate;

providing an opening in the sample film of the identified cell by a cutting device;

connecting a fluid unit to the cell via the opening;

supplying a fluid to the cell or extracting a fluid from the cell by the fluid unit.

14. Method according to claim 13, further comprising wherein the identifying takes place automatically based on markers on the multi-cell plate and/or based on image analysis by an identification device.

15. Method according to claim 13, wherein a fluid is supplied to the cell, the fluid influencing a crystallization process of a crystal comprised within the cell.

* * * * *